(12) United States Patent
Acosta et al.

(10) Patent No.: US 7,385,077 B1
(45) Date of Patent: Jun. 10, 2008

(54) FLUOROALKYL SURFACTANTS

(75) Inventors: Erick Jose Acosta, New Castle, DE (US); Stefan Reinartz, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/728,832

(22) Filed: Mar. 27, 2007

(51) Int. Cl.
C07C 229/00 (2006.01)
B01F 17/36 (2006.01)

(52) U.S. Cl. .................. 560/171; 560/172; 106/287.24

(58) Field of Classification Search ...................... None
See application file for complete search history.

(56) References Cited

U.S. PATENT DOCUMENTS

| | | | |
|---|---|---|---|
| 3,282,905 A | 11/1966 | Fasick et al. | |
| 3,575,961 A | 4/1971 | Tesoro et al. | |
| 3,719,698 A | 3/1973 | Tesoro et al. | |
| 3,849,401 A | 11/1974 | Tesoro et al. | |
| 4,473,371 A | 9/1984 | Schinzel et al. | |
| 4,993,448 A | 2/1991 | Karydas et al. | |
| 5,481,028 A | 1/1996 | Petrov et al. | |
| 6,747,169 B2 * | 6/2004 | Yanagi et al. ............... | 560/153 |
| 7,164,041 B1 | 1/2007 | Moore et al. | |
| 2006/0148671 A1 | 7/2006 | Dams et al. | |
| 2007/0049646 A1 | 3/2007 | Moore et al. | |

FOREIGN PATENT DOCUMENTS

| | | |
|---|---|---|
| DE | 32 33 830 A1 | 3/1984 |
| EP | 0 103 274 A2 | 3/1984 |
| EP | 0 319 951 A1 | 6/1989 |
| EP | 1 632 542 A1 | 3/2006 |
| JP | 2004083412 A | 3/2004 |
| JP | 2004098053 A | 4/2004 |
| WO | WO95/11877 | 5/1995 |

OTHER PUBLICATIONS

Balague et al., Synthesis of fluorinated telomers. Part 1. Telomerization of vinylidene fluoride with perfluoroalkyl iodides, J. of Fluorine Chemistry, 1995, 70 (2) 215-223.
Montefusco et al., Original vinylidene fluoride-containing acrylic monomers as surface modifiers in photopolymerized coatings; Macromolecules, 2004, 37(26), 9804-9813.

* cited by examiner

*Primary Examiner*—Paul A. Zucker

(57) ABSTRACT

Surfactants of formula (I)

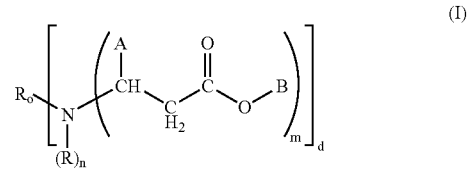

wherein
each R is independently hydrogen or a $C_1$ to $C_4$ alkyl group;
A is independently hydrogen or —C(O)—O—B;
$R_o$ is a linear, branched or cyclic aliphatic group, or combination thereof, having from about 2 to about 100 carbon atoms, interrupted or substituted by 1 to about 50 hydrophilic groups, said hydrophilic groups selected from the group consisting of hydroxyl, amino, ether and mixtures thereof; wherein specific ratios of and bonding of hydrophilic groups to carbon atoms is required;
each B is independently of specific formulae containing perfluoroalkyl and —S(CH$_2$)$_t$—, and m, d, n, and t are 0 or integers with specific limitations.

20 Claims, No Drawings

FLUOROALKYL SURFACTANTS

FIELD OF INVENTION

The field of invention is related to the synthesis and use of fluorochemical surfactants.

BACKGROUND OF INVENTION

For surfactants and surface treatment agents with fluorochemical chains, longer perfluoroalkyl chains contain a higher percentage of fluorine at a given concentration and typically provide better performance. However, the fluorinated materials derived from longer perfluoroalkyl chains are more expensive. Reduction of the fluorine content with delivery of the same or higher performance is therefore desirable. Reducing the fluorine content would reduce the cost, but it is necessary to maintain product performance.

U.S. Pat. No. 3,719,698 discloses the reaction of a primary alkyl amine with two equivalents of a fluorinated acrylate-type ester to provide an addition product useful as water and oil repellent finish for fabrics.

It is desirable to improve surfactant performance and to increase the fluorine efficiency, i.e., boost the efficiency or performance of the surfactants so a lower proportion of the expensive fluorine component is required to achieve the same level of performance, or to have better performance using the same level of fluorine. Especially desirable would be surfactants with similar performance to current commercial products but having shorter perfluoroalkyl tails. The present invention provides such surfactants.

SUMMARY OF INVENTION

The present invention comprises a composition of formula (I)

$$R_o \left[ N(R)_n \left( CH(A) CH_2 C(=O) O - B \right)_m \right]_d \quad (I)$$

wherein
m and d are each independently an integer of 1 or 2;
n is independently 0 or 1;
each R is independently hydrogen or a $C_1$ to $C_4$ alkyl group;
A is independently hydrogen or —C(O)—O—B;
$R_o$ is a linear, branched or cyclic aliphatic group, or combination thereof, having from about 2 to about 100 carbon atoms, interrupted or substituted by 1 to about 50 hydrophilic groups, said hydrophilic groups selected from the group consisting of hydroxyl, amino, ether and mixtures thereof; wherein the ratio of hydrophilic groups to carbon atoms is from about 1:1.1 to about 1:10, each carbon atom has at most one hydrophilic group bonded to it, and covalent bonding between hydrophilic groups is absent;
each B is independently a monovalent group of formula (IIa), (IIb) or (IIc):

$$R_f^1(CH_2)_t(R^1)_r— \quad (IIa)$$

$$R_f^2(CH_2CF_2)_p(CH_2CH_2)_q(R^1)_r— \quad (IIb)$$

$$R_f^3O(CF_2CF_2)_p(CH_2CH_2)_q(R^1)_r— \quad (IIc)$$

wherein
each of $R_f^1$ and $R_f^2$ are $C_1$-$C_6$ linear or branched perfluoroalkyl;
$R_f^3$ is a $C_1$ to $C_7$ linear or branched perfluoroalkyl group, optionally interrupted by one, two or three ether oxygen atoms;
t is an integer of 1 to about 10;
p and q are each independently integers of 1 to about 3;
r is 0 or 1;
$R^1$ is a divalent radical selected from —S(CH$_2$)$_t$—; and
provided that
when m is 1, n is 1;
when m is 2, n is 0, A is hydrogen, and d is 1; and
when d is 2, m is 1, A is —C(O)—O—B, $R_o$ has at least three carbon atoms, and nitrogens and hydrophilic groups are bonded to different carbon atoms.

The present invention further comprises a method of lowering surface tension of a medium comprising contacting the medium with a composition of formula (I) as defined above.

The present invention further comprises a method of providing resistance to blocking, open time extension, and leveling to a coated substrate comprising adding to the coating base prior to deposition on the substrate, a composition comprising one or more compounds of formula (I) as described above wherein $R_o$ is $R_o^1$, wherein $R_o^1$ is a linear or branched aliphatic group, or combination thereof, of from about 10 to about 100 carbon atoms interrupted by from about 5 to about 50 ether oxygen atoms, wherein the ratio of ether oxygen atoms to carbon atoms is from about 1:2 to about 1:3; and wherein each carbon atom has at most one ether oxygen atom bonded to it, and covalent bonding between ether oxygen atoms is absent.

The present invention further comprises a substrate to which has been applied a composition of formula (I) as described above with the proviso that $R_o$ is $R_o^1$.

DETAILED DESCRIPTION

Herein all trademarks are designated with capital letters.

All patents cited herein are hereby incorporated by reference.

The present invention provides surfactants having increased fluorine efficiency compared to available commercial products. A lower proportion of fluorine is required to achieve the same level of performance, or better performance is obtained using the same level of fluorine. This is achieved in that the compounds of the invention contain shorter perfluoroalkyl groups.

The present invention comprises compounds of formula (I)

$$R_o \left[ N(R)_n \left( CH(A) CH_2 C(=O) O - B \right)_m \right]_d \quad (I)$$

wherein
m and d are each independently an integer of 1 or 2;
n is independently 0 or 1;
each R is independently hydrogen or a $C_1$ to $C_4$ alkyl group;
A is independently hydrogen or —C(O)—O—B;

$R_o$ is a linear, branched or cyclic aliphatic group, or combination thereof, having from about 2 to about 100 carbon atoms, interrupted or substituted by 1 to about 50 hydrophilic groups, said hydrophilic groups selected from the group consisting of hydroxyl, amino, ether and mixtures thereof; wherein the ratio of hydrophilic groups to carbon atoms is from about 1:1.1 to about 1:10; each carbon atom has zero or one hydrophilic group bonded to it; and covalent bonding between hydrophilic groups is absent;

each B is independently a monovalent group of formula (IIa), (IIb) or (IIc):

  (IIa)

  (IIb)

  (IIc)

wherein
each of $R_f^1$ and $R_f^2$ are $C_1$-$C_6$ linear or branched perfluoroalkyl;

$R_f^3$ is a $C_1$ to $C_7$ linear or branched perfluoroalkyl group, optionally interrupted by one, two or three ether oxygen atoms;

t is an integer of 1 to about 10;

p and q are each independently integers of 1 to about 3;

r is 0 or 1;

$R^1$ is a divalent radical selected from —S(CH$_2$)$_t$—; and provided that when m is 1, n is 1;

when m is 2, n is 0, A is hydrogen, and d is 1; and when d is 2, m is 1, A is —C(O)—O—B, $R_o$ has at least three carbon atoms, and the nitrogen atoms and hydrophilic groups are bonded to different carbon atoms.

Within the group $R_o$, the ratio of hydrophilic groups to carbon atoms is from about 1:1.1 to about 1:10. Preferably this ratio is from about 1:1.1 to about 1:5, more preferably from about 1:1.1 to about 1:4.

Within the group $R_o$ each carbon atom has zero or one hydrophilic group bonded to it, and covalent bonding between the hydrophilic groups is absent. This means that no covalent bonding exists between any hydrophilic groups, but hydrogen bonding between hydrophilic groups is possible. For example, hydrogen bonding can exist between a hydrophilic hydroxyl group and an ether oxygen. However, covalent oxygen-oxygen bonding and oxygen-nitrogen bonding does not exist (is absent).

One embodiment of the invention is a composition of formula (I) as defined above wherein m is 2, n is 0, A is hydrogen, and d is 1, herein denoted as formula (Ia).

  (Ia)

These materials are prepared by addition of primary amines, $R_o$—NH$_2$, to fluorinated acrylate esters according to Path A in Reaction Scheme 1 below. A monoamine requires about two equivalents of fluorinated acrylate ester to provide the desired products of formula (Ia). The addition reaction typically can be accomplished in the absence of solvent or additional catalyst. However, a solvent, for instance, toluene, tetrahydrofuran, acetonitrile or other suitable solvent can be used. A catalyst, for instance, a tertiary amine, such as triethyl amine can be used, if so desired. Preferably the addition reaction is performed at elevated temperature, for instance, 40 to 80° C. The product of the addition reaction usually comprises about 80 to about 92% of the bis-adduct of formula (Ia) with the remainder being the mono-adduct intermediate, and residual fluorinated acrylate. Gas chromatography (GC) is used to monitor the reaction and the purity of the products.

Reaction Scheme 1

Path A

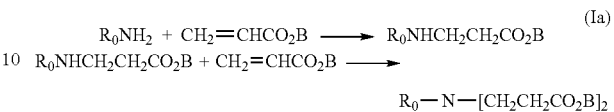  (Ia)

Path B

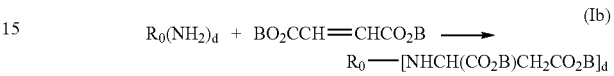  (Ib)

Another embodiment of the invention is a composition of formula (I) wherein m is 1, n is 1, and A is —C(O)—O—B, herein denoted as formula (Ib).

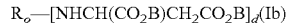(Ib)

These materials are prepared by addition of primary amines, $R_o$—(NH$_2$)$_d$, to maleate esters according to Path B outlined in Reaction Scheme 1 above. A monoamine (wherein d is 1) requires about one equivalent of fluorinated maleate ester; and a diamine (wherein d is 2) requires about two equivalents of fluorinated maleate ester, to provide the desired products of formula (Ib). The preferred reaction conditions are those described above for compositions of formula (Ia). The addition reaction can be monitored by liquid chromatography/mass spectrometry (LC/MS) or gas chromatography (GC).

Another embodiment of the invention is a composition of formula (I) wherein the nitrogen (or nitrogens, when d=2) is from about 40 mol % to 100 mol % salinized. The term "wherein the nitrogen is from about 40 mol % to 100 mol % salinized" means that the nitrogen atom of formula (I) may be present in a protonated or alkylated form or a partially protonated or partially alkylated form. The salinization of the nitrogen of formula (I) provide useful water dispersibility and/or solubility properties to the compositions of formula (I). A convenient and preferred approach to providing partially or fully salinized compositions of formula (I) comprises adding an acid to the composition. Examples of such acids are hydrochloric, hydrobromic, sulfuric, nitric, phosphoric, acetic, formic, propionic or lactic acids. Preferably, acetic acid is used, and preferably the nitrogen(s) are fully salinized. Preferably water is present as a solvent for the acid. Full salinization can be accomplished by using from about 1 to about 2 equivalents of acid per nitrogen, based on the equivalents of composition of formula (I).

Partial or full salinization can be used to purify the compositions of the invention. For instance, acetic acid is added to the compositions, to form an acid solution that is extracted with a solvent, such as hexane. The solvent extraction is used to remove residual fluorinated acrylate or fluorinated maleate esters, thus increasing the purity of the compositions of the invention.

Another embodiment of this invention is a composition of formula (I) wherein d is 1 and $R_o$ is a linear, branched or cyclic aliphatic group, or combination thereof, having from about 2 to about 10 carbon atoms, interrupted or substituted by one hydroxyl, ether or tertiary amino group. Preferred are those compositions of formula (I), and especially preferred are those of formula (Ia), wherein $R_o$— is selected from the group consisting of:

—$CH_2CH_2CH_2OH$;

—$CH_2CH(OH)CH_3$;

—$CH_2CH_2CH_2CH_2OH$;

—$CH_2CH_2CH_2CH_2CH_2CH_2OH$;

—$CH_2CH_2N(CH_3)_2$;

—$CH_2CH_2CH_2N(CH_3)_2$;

—$CH_2CH_2CH_2CH_2N(CH_3)_2$;

—$CH_2CH_2N(CH_2CH_3)_2$;

—$CH_2CH_2CH_2N(CH_2CH_3)_2$; and

—$CH_2CH_2CH_2CH_2N(CH_2CH_3)_2$.

These compositions are useful as surfactants in aqueous media in their salinized form.

Other preferred compositions of formula (I) are those wherein $R_o$ is $R_o^1$. $R_o^1$ is a subset of $R_o$ and is a linear or branched aliphatic group, or combination thereof, of about 10 to about 100 carbon atoms interrupted by about 5 to about 50 ether oxygens, and more preferably about 20 to 40 carbon atoms interrupted by about 5 to about 20 ether oxygen, wherein the ratio of ether oxygen atoms to carbon atoms is from about 1:2 to about 1:4; and more preferably, from about 1:2 to about 1:3 and wherein each carbon atom has at most one ether oxygen atom bonded to it, and covalent bonding between ether oxygen atoms is absent. Within these compositions, preferably $R_o^1$ has a molecular weight, when each valency is occupied by an —$NH_2$ group, of between about 200 to about 2200, and a solubility in water of 1% by weight, and more preferably 5% by weight, or higher. These materials are provided by reaction of amine-terminated polyoxyalkylenes with fluorinated acrylates and fluorinated maleates.

Amine-terminated polyoxyalkylenes useful in the formation of compositions of formula (Ia) and formula (Ib) include amine-terminated polyethylene glycol monomethyl ether (mPEGNH$_2$) or amine terminated polyethylene glycol-polypropylene glycol-polyethylene glycol triblock monomethyl ether (mPEG-PPG-PEG-NH$_2$). They are available by treatment of corresponding hydroxyl terminated monomethyl ethers with thionyl bromide followed by treatment with ammonia as described by Bückmann et al (Makromol. Chem. 182, p. 1379-1384, 1981). In a similar manner amine terminated monomethyl ethers of random copolymers of ethylene oxide and propylene oxide are also available. Commercial examples of these materials are JEFFAMINE polyoxyalkyleneamines XTJ-505, and XTJ-506 from Huntsman Chemical, Salt Lake City, Utah, and a development sample XTJ-580, also known as SURFONAMINE L-55 and available from Huntsman Chemical, Salt Lake City, Utah.

Other amine-terminated polyoxyalkylenes useful in the formation of compositions of formula (Ib) include amine terminated polyethylene glycol ethers (NH$_2$—PEG-NH$_2$), amine terminated polyethylene glycol-polypropylene glycol-polyethylene glycol triblock ethers (NH$_2$—PEG-PPG-PEG-NH$_2$) and amine terminated random copolymers of ethylene oxide and propylene oxide. They are available by synthesis by treatment of the corresponding hydroxy terminated polymers with thionyl chloride and ammonia. Commercial examples of these materials are JEFFAMINE polyoxyalkyleneamines ED-600 (XTJ-500, MW 600), ED-900 (XTJ-501, MW 900), ED-2003 (XTJ-502, MW 2000), and HK-511 (MW 220) available from Huntsman Chemical, Salt Lake City, Utah.

Preferably the amine-terminated polyoxyalkylenes have from about 5 to about 20 repeat units, and more preferably from about 10 to about 20 repeat units. Preferred amine-terminated polyoxyalkylenes for preparing compositions of the invention have a water solubility of 1% by weight, and more preferably a water solubility of 5% by weight, or higher. These materials typically are predominately polyethylene glycol (PEG) based and are therefore more hydrophilic than polypropylene glycol (PPG) based materials.

Compositions of formula (Ia) and (Ib), wherein $R_o$ is $R_o^1$, exhibit good surfactant properties in aqueous media at about neutral to slightly basic pH, for instance, between about pH of 6 and about pH of 9, and higher. Thus, they are useful as surfactants and surface treatment agents in a wide variety of commercial formulations including many latex-based formulations that use anionic or nonionic surfactants or a mixture thereof.

Another embodiment of the invention is a composition of formula (I) wherein B is selected from the group consisting of $R_f^1(CH_2)_t(R^1)_r$—, formula (IIa). In this embodiment preferably $R_f^1$ is $C_4$-$C_6$ linear or branched perfluoroalkyl; t is from about 2 to about 4; and r is 0.

Another embodiment of the invention is a composition of formula (I) wherein B is selected from the group consisting of $R_f^2(CH_2CF_2)_p(CH_2CH_2)_q(R^1)_r$—, formula (IIb). In this embodiment preferably $R_f^2$ is a $C_4$-$C_6$ linear or branched perfluoroalkyl; p and q are each independently 1 or 2; and r is 0. Another embodiment of the invention is a composition of formula (I) wherein B is selected from the group consisting of $R_f^3O(CF_2CF_2)_p(CH_2CH_2)_q(R^1)_r$—, formula (IIc). In this embodiment preferably $R_f^3$ is a $C_3$ to $C_7$ linear or branched perfluoroalkyl, optionally interrupted by one, two or three ether oxygen atoms; p and q are each independently 1 or 2; and r is 0.

The fluorinated acrylates useful in forming compositions formula (Ia) of the invention are prepared from the corresponding fluorinated alcohols by esterification with acrylic acid, using procedures as described in U.S. Pat. No. 3,282,905 and European Patent 1632542 A1. Alternatively, fluorinated acrylate esters can be made from the corresponding nitrate esters according to the procedures disclosed in U.S. Pat. No. 3,890,376. The fluorinated maleates useful in forming compositions of formula (Ib) the invention are prepared from the corresponding fluorinated alcohols by esterification of maleic anhydride.

Fluorinated alcohols useful in forming fluorinated acrylates and fluorinated maleates useful in the invention include those of formulas (IIIa), (IIIb) and (IIIc):

  (IIIa)

  (IIIb)

  (IIIc)

In formula (IIIa) the perfluoroalkyl group preferably is linear, although compositions containing branched-chain perfluoroalkyl groups are suitable. The perfluoroalkylethanols, wherein t=2, and $R_f^1$ has 2 or 6 carbon atoms, are available by fractional distillation of the commercially available telomer mixture of perfluoroalkylethanols. Specific fluorinated alcohols of formula (IIIa) that are commercially available include 1H,1H,2H,2H-perfluoro-1-hexanol and 1H,1H,2H,2H-perfluoro-1-octanol.

Fluorinated telomer alcohols of formula (IIIb), wherein $R_f^2$ is a linear or branched perfluoroalkyl group having 1 to 6 carbon atoms, are available by synthesis according to Reaction Scheme 2.

Fluorinated alcohols of formula (IIIc), wherein p=1 and $R_f^3$ is a linear or branched perfluoroalkyl group having 2 to 7 carbon atoms optionally interrupted by one, two or three ether oxygen atoms, are available by synthesis according to Reaction Scheme 3.

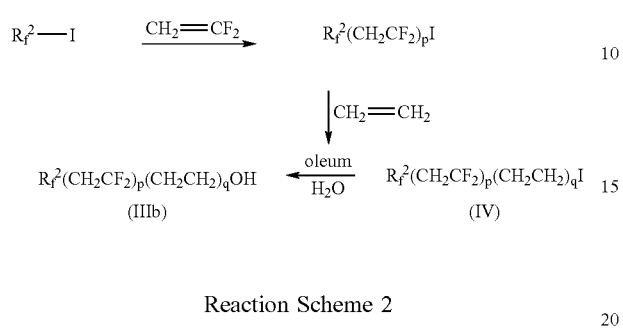

Reaction Scheme 2

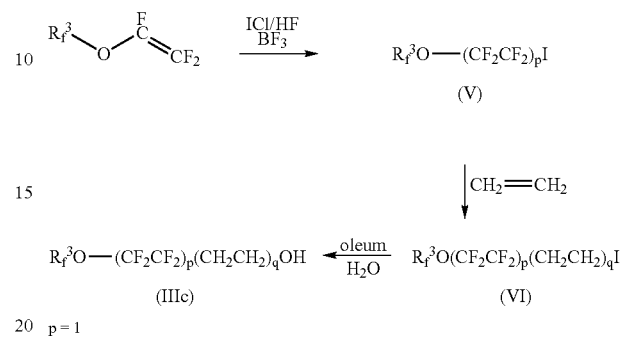

p = 1

Reaction Scheme 3

The telomerization of vinylidene fluoride (VDF) with linear or branched perfluoroalkyl iodides is well known, and produces compounds of the structure $R_f^2(CH_2CF_2)_pI$, wherein, p is 1 or more and $R_f^2$ is a C1 to C6 perfluoroalkyl group. For example, see Balague, et al, "Synthesis of fluorinated telomers, Part 1, Telomerization of vinylidene fluoride with perfluoroalkyl iodides", J. Fluor. Chem. (1995), 70(2), 215-23; and Montefusco, et al, "Original Vinylidene Fluoride-Containing Acrylic Monomers as Surface Modifiers in Photopolymerized Coatings", Macromolecules (2004), 37(26), 9804-9813. The specific telomer iodides are isolated by fractional distillation. The telomer iodides can be treated with ethylene by procedures described in U.S. Pat. No. 3,979,469, to provide the telomer ethylene iodides (IV) wherein q is 1 to 3 or more. The telomer ethylene iodides (IV) can be treated with oleum and hydrolyzed to provide the corresponding telomer alcohols (IIIb) according to procedures disclosed in WO 95/11877. Alternatively, the telomer ethylene iodides (IV) can be treated with N-methyl formamide followed by ethyl alcohol/acid hydrolysis.

Specific examples of fluorinated telomer alcohols (IIIa), and (IIIb) derived from telomerization of vinylidene fluoride and ethylene, and useful in forming fluorinated acrylates useful in the invention include those listed in Table 1A. The groups $C_3F_7$, $C_4F_9$, and $C_6F_{13}$, referred to in the list of specific alcohols, in Tables 1A and 1B, and in the examples herein, refer to linear perfluoroalkyl groups unless specifically indicated otherwise.

TABLE 1A

| Compound | Structure |
| --- | --- |
| A1 | $C_4F_9CH_2CH_2OH$, |
| A2 | $C_4F_9(CH_2CH_2)_2OH$, |
| A3 | $C_6F_{13}CH_2CH_2OH$, |
| A4 | $C_6F_{13}(CH_2CH_2)_2OH$, |
| A5 | $C_6F_{13}(CH_2CH_2)_3OH$, |
| A6 | $C_4F_9CH_2CF_2CH_2CH_2OH$, |
| A7 | $C_4F_9(CH_2CF_2)_2CH_2CH_2OH$, |
| A8 | $C_4F_9(CH_2CF_2)_3CH_2CH_2OH$, |
| A9 | $C_4F_9CH_2CF_2(CH_2CH_2)_2OH$, |
| A10 | $C_4F_9(CH_2CF_2)_2(CH_2CH_2)_2OH$, |
| A11 | $C_6F_{13}CH_2CF_2CH_2CH_2OH$, |
| A12 | $C_6F_{13}(CH_2CF_2)_2CH_2CH_2OH$, |
| A13 | $C_6F_{13}(CH_2CF_2)_3CH_2CH_2OH$, |
| A14 | $C_6F_{13}CH_2CF_2(CH_2CH_2)_2OH$, |
| A15 | $C_6F_{13}(CH_2CF_2)_2(CH_2CH_2)_2OH$. |

The perfluoroalkyl ether iodides (V) are made by the procedure described in Example 8 of U.S. Pat. No. 5,481,028, using perfluoroalkyl vinyl ethers as a starting material. In the second reaction in Scheme 2, the perfluoroalkyl ether iodide (V) is reacted with an excess of ethylene at an elevated temperature and pressure to provide telomer ethyl iodide (VI). While the addition of ethylene can be carried out thermally, the use of a suitable catalyst is preferred. Preferably the catalyst is a peroxide catalyst such as benzoyl peroxide, isobutyroyl peroxide, propionyl peroxide, or acetyl peroxide. More preferably the peroxide catalyst is benzoyl peroxide. The temperature of the reaction is not limited, but a temperature in the range of 110° C. to 130° C. is preferred. The reaction time may vary with the catalyst and reaction conditions, but we have found 24 hours (h) to be adequate. The product is purified by any means that separates unreacted starting material from the final product, but distillation is preferred. Satisfactory yields up to 80% of theory have been obtained using about 2.7 mols of ethylene per mole of perfluoroalkyl ether iodide, a temperature of 110° C. and autogenous pressure, a reaction time of 24 h, and purifying the product by distillation. The perfluoroalkylether ethyl iodides (VI) are treated with oleum and hydrolyzed to provide the corresponding alcohols (IIIc) according to procedures disclosed in WO 95/11877. Alternatively, the perfluoroalkylether ethyl iodides are treated with N-methyl formamide followed by ethyl alcohol/acid hydrolysis.

The higher homologs of (IIIc) wherein p is 2 or 3 are available by telomerization of tetrafluoroethylene with the perfluoroalkyl ether iodides (V) wherein p is 1, followed by isolation of specific telomers by distillation, and then telomerization with ethylene. The higher homologs (q is 2 or 3) of telomer ethylene iodides are available by reaction with excess ethylene at high pressure.

Specific examples of fluorinated alcohols (IIIc) useful in forming fluorinated acrylates and maleates useful in the invention include those listed in Table 1B

TABLE 1B

| Compound | Structure |
| --- | --- |
| B1 | $C_2F_5OCF_2CF_2CH_2CH_2OH$, |
| B2 | $C_2F_5O(CF_2CF_2)_2CH_2CH_2OH$, |
| B3 | $C_3F_7OCF_2CF_2CH_2CH_2OH$, |
| B4 | $C_3F_7O(CF_2CF_2)_2CH_2CH_2OH$, |
| B5 | $C_4F_9OCF_2CF_2CH_2CH_2OH$, |
| B6 | $C_4F_9O(CF_2CF_2)_2CH_2CH_2OH$, |
| B7 | $C_6F_{13}OCF_2CF_2CH_2CH_2OH$, |
| B8 | $C_6F_{13}O(CF_2CF_2)_2CH_2CH_2OH$, |
| B9 | $CF_3OCF(CF_3)CF_2OCF_2CF_2CH_2CH_2OH$, |
| B10 | $CF_3OCF(CF_3)CF_2O(CF_2CF_2)_2CH_2CH_2OH$, |
| B11 | $C_2F_5OCF(CF_3)CF_2OCF_2CF_2CH_2CH_2OH$, |
| B12 | $C_2F_5OCF(CF_3)CF_2O(CF_2CF_2)_2CH_2CH_2OH$, |
| B13 | $C_3F_7OCF(CF_3)CF_2OCF_2CF_2CH_2CH_2OH$, |
| B14 | $C_3F_7OCF(CF_3)CF_2O(CF_2CF_2)_2CH_2CH_2OH$. |

Another embodiment of the invention is a composition of formula (I) wherein within formulas (IIa), (IIb) and (IIc), r is 1, and $R^1$ is a divalent radical selected from —S—$(CH_2)_t$—. This is a linking group that is optionally present in the compositions of the invention. In this embodiment the sulfur atom of the linking group is bonded to only carbon atoms. Fluorinated alcohols useful in forming fluorinated acrylates and fluorinated maleates wherein r is 1 include those of formulas (VIIa), (VIIb) and (VIIc):

$$R_f^1(CH_2)_rS(CH_2)_tOH \qquad (VIIa)$$

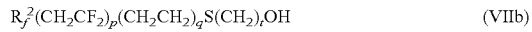

$$R_f^2(CH_2CF_2)_p(CH_2CH_2)_qS(CH_2)_tOH \qquad (VIIb)$$

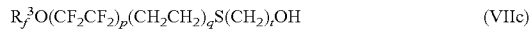

$$R_f^3O(CF_2CF_2)_p(CH_2CH_2)_qS(CH_2)_tOH \qquad (VIIc)$$

Fluorinated alcohols (VIIb) and (VIIc) are prepared by synthesis from the ethylene iodides of formula (IV) and (VI), respectively, by reaction with omega-mercapto-alkanols, for instance, 2-mercaptoethanol. Fluorinated alcohols of formula (VIIa) are available in an analogous manner from $R_f^1(CH_2)_tI$, that are commercially available.

Partially or fully salinized compositions of formula (I) are useful surfactants in acidic or slightly acidic media, for instance. A comparison of surface tension stability in slightly acidic media over a period of time at ambient temperature, indicate that compositions of formula (I) wherein $R_f$ may vary, has the following order of stability: (IIb)>(IIc)>(IIa). Thus, for applications where a maximum degree of surfactant stability is required, compositions of formula (I) wherein $R_f$ is (IIb) are preferred. For applications wherein a minimum degree of surfactant stability is desirable, for instance, in some environmental applications wherein degradability is desirable, compositions of formula (I) wherein $R_f$ is (IIa) are preferred. While not wishing to be bound by theory, for the purpose of understanding the preferences, the difference in stability in acidic media may be a result of the different hydrolytic stability of fluorinated esters in acidic media. Furthermore, in using the surfactants of the invention, it may be desirable for certain applications to salinize the compositions of formula (I) before use.

The present invention further comprises a method of lowering surface tension of a medium comprising contacting the medium with a composition of formula (I) as defined above. Any of a wide variety of media are suitable for use in the method of the present invention. Typically the medium is a liquid. Examples of suitable medium include, for example, a coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, or bonding agent. Adding a composition of the present invention to the medium results in lowering the surface tension of the medium due to the surfactant properties of the composition of the present invention. The composition of the present invention is typically simply blended with or added to the medium.

The present invention further comprises a method of providing resistance to blocking, open time extension, and leveling to a coated substrate comprising adding to the coating base prior to deposition on the substrate, a composition comprising one or more compounds of formula (I) as described above wherein $R_o$ is $R_o^1$. $R_o^1$ is a subset of $R_o$, and is a linear or branched aliphatic group, or combination thereof, of from about 10 to about 100 carbon atoms interrupted by from about 5 to about 50 ether oxygen atoms, wherein the ratio of ether oxygen atoms to carbon atoms is from about 1:2 to about 1:3; and wherein each carbon atom has at most one ether oxygen atom bonded to it, and covalent bonding between ether oxygen atoms is absent. Within the group $R_o^1$ each carbon atom has zero or one ether oxygen atom bonded to it, and covalent bonding between ether oxygen atoms is absent. This means that no covalent bonding exists between any of the ether oxygen atoms. Compositions of formula (I) as disclosed above wherein $R_o$ is $R_o^1$ are useful as surfactants in neutral or slightly basic media, for instance, between from about pH of 6 to about pH of 9.

Suitable coating compositions, referred to herein by the term "coating base", include a composition, typically a liquid formulation, of an alkyd coating, Type I urethane coating, unsaturated polyester coating, or water-dispersed coating, and is applied to a substrate for the purpose of creating a lasting film on the substrate surface. These are conventional paints, stains, and similar coating compositions.

By the term "alkyd coating" as used herein is meant a conventional liquid coating based on alkyd resins, typically a paint, clear coating, or stain. The alkyd resins are complex branched and cross-linked polyesters containing unsaturated aliphatic acid residues. Conventional alkyd coatings utilize, as the binder or film-forming component, a curing or drying alkyd resin. Alkyd resin coatings contain unsaturated aliphatic acid residues derived from drying oils. These resins spontaneously polymerize in the presence of oxygen or air to yield a solid protective film. The polymerization is termed "drying" or "curing" and occurs as a result of autoxidation of the unsaturated carbon-carbon bonds in the aliphatic acid component of the oil by atmospheric oxygen. When applied to a surface as a thin liquid layer of formulated alkyd coating, the cured films that form are relatively hard, non-melting, and substantially insoluble in many organic solvents that act as solvents or thinners for the unoxidized alkyd resin or drying oil. Such drying oils have been used as raw materials for oil-based coatings and are described in the literature.

By the term "urethane coating" as used hereinafter is meant a conventional liquid coating based on Type I urethane resins, typically a paint, clear coating, or stain. Urethane coatings typically contain the reaction product of a polyisocyanate, usually toluene diisocyanate, and a polyhydric alcohol ester of drying oil acids. Urethane coatings are classified by ASTM D-1 into five categories. Type I urethane coatings contain a pre-reacted autoxidizable binder as described in Surface Coatings Vol. 1, previously cited. These are also known as uralkyds, urethane-modified alkyds, oil-modified urethanes, urethane oils, or urethane alkyds, are the largest volume category of polyurethane coatings and include paints, clear coatings, or stains. The cured coating is formed by air oxidation and polymerization of the unsaturated drying oil residue in the binder.

By the term "unsaturated polyester coating" as used hereinafter is meant a conventional liquid coating based on unsaturated polyester resins, dissolved in monomers and containing initiators and catalysts as needed, typically as a paint, clear coating, or gel coat formulation. Unsaturated polyester resins contain as the unsaturated prepolymer the product obtained from the condensation polymerization of a glycol such as 1,2-propylene glycol or 1,3-butylene glycol with an unsaturated acid such as maleic (or of maleic and a saturated acid, e.g., phthalic) in the anhydride form. The unsaturated prepolymer is a linear polymer containing unsaturation in the chain. This is dissolved in a suitable monomer, for instance styrene, to produce the final resin. The film is produced by copolymerization of the linear polymer and monomer by means of a free radical mechanism. The free radicals can be generated by heat, or more usually by addition of a peroxide, such as benzoyl peroxide, separately packaged and added before use. Such coating compositions are frequently termed "gel coat" finishes. For curing coatings at room temperature, the decomposition of peroxides into free radicals is catalyzed by certain metal ions, usually cobalt. The solutions of peroxide and cobalt compound are added separately to the mix and well stirred before application. The unsaturated polyester resins that cure by a free radical mechanism are also suited to irradiation curing using, for instance, ultraviolet light. This form of cure, in which no heat is produced, is particularly suited to films on wood or board. Other radiation sources, for instance electron-beam curing, are also used.

By the term "water-dispersed coatings" as used herein is meant coatings intended for the decoration or protection of a substrate composed of water as an essential dispersing component such as an emulsion, latex, or suspension of a film-forming material dispersed in an aqueous phase. "Water-dispersed coating" is a general classification that describes a number of formulations and includes members of the above described classifications as well as members of other classifications. Water-dispersed coatings in general contain other common coating ingredients. Water-dispersed coatings are exemplified by, but not limited to, pigmented coatings such as latex paints, unpigmented coatings such as wood sealers, stains, and finishes, coatings for masonry and cement, and water-based asphalt emulsions. A water dispersed coating optionally contains surfactants, protective colloids and thickeners, pigments and extender pigments, preservatives, fungicides, freeze-thaw stabilizers, antifoam agents, agents to control pH, coalescing aids, and other ingredients. For latex paints the film forming material is a latex polymer of acrylate acrylic, vinyl-acrylic, vinyl, or a mixture thereof. Such water-dispersed coating compositions are described by C. R. Martens in "Emulsion and Water-Soluble Paints and Coatings" (Reinhold Publishing Corporation, New York, N.Y., 1965).

By the term "dried coating" as used herein is meant the final decorative and/or protective film obtained after the coating composition has dried, set or cured. Such a final film can be achieved by, for non-limiting example, curing, coalescing, polymerizing, interpenetrating, radiation curing, UV curing or evaporation. Final films can also be applied in a dry and final state as in dry coating.

Blocking is the undesirable sticking together of two coated surfaces when pressed together, or placed in contact with each other for an extended period of time. When blocking occurs separation of the surfaces can result in disruption of the coating on one or both surfaces. Thus improved resistance to blocking is beneficial in many situations where two coated surfaces need to be in contact, for example on window frames.

The term "open time extension" is used herein to mean the time period during which a layer of liquid coating composition can be blended into an adjacent layer of liquid coating composition without showing a lap mark, brush mark, or other application mark. It is also called wet-edge time. Latex paints containing low boiling, volatile organic chemicals (VOC) have shorter than desired open-time due to lack of high boiling temperature VOC solvents. Lack of open time extension will cause surface defects such as overlapping brush marks or other marks. A longer open time extension is beneficial when the appearance of the coated surface is important, as it permits application of the coating without leaving overlap marks, brush marks, or other application marks at the area of overlap between one layer of the coating and an adjacent layer of the coating.

When used as additives to a coating base the compositions of the present invention of formula (I) wherein $R_o$ is $R_o^1$ as defined above are effectively introduced to the coating base or other composition by thoroughly stirring it in at room or ambient temperature. More elaborate mixing can be employed such as using a mechanical shaker or providing heat or other methods. Such methods are not necessary and do not substantially improve the final composition. When used as an additive to latex paints, the compositions of the invention generally are added at about 0.001 weight % to about 5 weight % by dry weight of the composition of the invention in the wet paint. Preferably about from about 0.01 weight % to about 1 weight %, and more preferably from about 0.1 weight % to about 0.5 weight % is used.

The composition of the present invention is useful as a surfactant in a wide variety of media. It is further useful to alter the surface properties of such media. For example, surface properties such as surface tension, leveling, open time extension, and blocking are altered by adding the composition of the present invention to the media. The compositions of the present invention have enhanced fluorine efficiency compared to current commercial products. The inventive compositions provide the advantages of altering surface properties using less fluorine to achieve the same level of performance, or provide better performance using the same level of fluorine, as prior art compositions.

Test Methods

The following test methods were use in the examples herein.

Test Method 1—Surface Tension Measurement

Test Method 1A.

The surface tension measurements of the surfactants were measured in 1% by weight acetic acid in deionized water using the Wilhelmy plate method on an automated Krüss tensiometer (Model K11, Krüss USA, Nazareth, Pa.) used in accordance with the manufacturers' manuals. The samples were initially prepared at 1% by weight concentrations and diluted with deionized water in the following series: 0.5, 0.1, 0.05, 0.01, 0.005, 0.0025, 0.001, and 0.0005% by weight. Lower surface tension values at a given concentration denote improved surfactant properties.

Test Method 1B

The surface tension measurements of the surfactants were measured in fresh MILLIPORE filtered water using the Wilhelmy plate method on an automated Krüss tensiometer (Model K11, Krüss USA, Nazareth, Pa.) or a Sigma70 tensiometer (KSV Instruments Inc., Monroe, Conn.) used in accordance with the manufacturers' manuals. MILLIPORE filters are available from Millipore Corporation, Billerica, Mass. The samples were initially prepared at 1 wt % concentrations and diluted in the following series: 0.5, 0.1, 0.05, 0.01, 0.005, 0.0025, 0.001, and 0.0005% by weight. All vessels were cleaned and rinsed thoroughly first with tap water, then deionized water, then triple rinsed with MILLIPORE filtered water. After the measurements beakers were dried, and they were optionally cleaned in a plasma cleaning oven for 5 minutes.

Test Method 2—Wetting and Leveling Test

To test the performance of the samples in their wetting and leveling ability, the samples were added to a floor polish (RHOPLEX 3829, supplied by Rohm & Haas, Spring House, Pa., was used to prepare the final testing formulation) and applied to half of a stripped 12 inch×12 inch (30.36 cm×30.36 cm) vinyl tile. A 1% by weight solution of the surfactant to be tested was prepared by dilution in deionized water. Following the manufacturer protocols, a 100 g portion of the RHOPLEX 3829 formulation was prepared, followed by addition of 0.75 g of the 1% by weight surfactant solution, to provide a test floor polish.

The test floor polish was applied to a tile by placing 3 mL portion of the test polish in the center of the tile, and spreading from top to bottom using an applicator, and finally placing a large "X" across the tile, using the applicator. The tile was allowed to dry for 30 min and a total of 5 coats were applied. After each coat, the tile was rated on a 1 to 5 scale (1 being the worst, 5 the best) on the surfactant's ability to promote wetting and leveling of the polish on the tile surface. The rating was determined based on comparison of a tile treated with the floor polish that contained no added surfactant according to the following scale:

| | Subjective Tile Rating Scale |
|---|---|
| 1 | Uneven surface coverage of the film, significant streaking and surface defects |
| 2 | Visible streaking and surface defects, withdrawal of the film from the edges of the tile |
| 3 | Numerous surface defects and streaks are evident but, generally, film coats entire tile surface |
| 4 | Minor surface imperfections or streaking |
| 5 | No visible surface defects or streaks |

Test Method 3—Open-Time Extension

Open-time is time during which a layer of applied liquid coating composition can be blended into an adjacent layer of liquid coating composition without showing a lapmark, brush mark, or other application mark. It is also called wet-edge time. Low VOC latex paint has shorter than desired open-time due to lack of high boiling temperature VOC solvents. Lack of sufficient open-time will result in overlapping brush marks or other marks. Open-time testing is conducted by a well-accepted industry practice, called thumb press method as described herein. A double strip drawdown panel of the control sample and the sample with 0.1% active ingredient of the sample to be tested was employed. The coating composition to be tested and the control were the same coating composition wherein the control contained no additive to be tested, and the sample to be tested contained a composition of the present invention as an additive. The panel was made with a 7 cm doctor blade at 20-25° C. and 40-60% relative humidity. A double thumb press with equal pressure was then applied to each sample side by side at 1-2 minute intervals. The end point was when no paint residue on the thumb was observed. The time from when the drawdown was made to the end point was recorded as open-time. The percent difference between the control and sample containing the additive was recorded as the percent open-time extension. Compositions of the present invention were tested in a semi-gloss latex paint.

Test Method 4—Blocking Resistance of Architectural Latex Paints

The test method described herein is a modification of ASTM D4946-89—Standard Test Method for Blocking Resistance of Architectural Paints, which is hereby specifically incorporated by reference.

The face-to-face blocking resistance of paints to be tested was evaluated in this test. Blocking, for the purpose of this test, is defined as the undesirable sticking together of two painted surfaces when pressed together or placed in contact with each other for an extended period of time.

The paint to be tested was cast on a polyester test panel using the applicator blade. All painted panels were protected from surface contamination, such as grease, oil, fingerprints, dust, and the like. Typically, results were sought at 24 hours after casting the paint. After the panels had been conditioned in the conditioned room as specified in the test method for the desired period of time, six squares (3.8 cm×3.8 cm) were cut out from the painted test panel. The cut sections (three pairs) were placed with the paint surfaces face-to-face for each of the paints to be tested. The face-to-face specimens were placed in a 50° C. oven on a marble tray. A no. 8 stopper was placed on top, with the smaller diameter in contact with the specimens, and then a 1000 g weight was placed on top of the stopper. This resulted in a pressure of 1.8 psi (12,400 Pascal) on the specimens. One weight and stopper was used for each specimen tested. After exactly 30 minutes, the stoppers and weights were taken off the test specimens which were removed from the oven and allowed to cool in the conditioned room for 30 minutes before determining the block resistance.

After cooling, the specimens were separated by peeling apart with a slow and steady force. The blocking resistance was rated from 0 to 10, corresponding to a subjective tack assessment (sound made upon separation of the painted specimens) or seal (complete adhesion of the two painted surfaces) as determined by the operator of the method. The specimen was put near the ear to actually hear the degree of tack. The rating system is described in the Table entitled Blocking Resistance Numerical Ratings below. The degree of seal was estimated from the appearance of the specimens and the fraction of the paint surfaces that adhere. Paint tearing away from the test panel backing was an indication of seal. A higher number indicated better resistance to blocking.

| Blocking Resistance Numerical Ratings | | |
|---|---|---|
| Blocking Resistance Numerical Ratings | Description of the Separation | Performance Description |
| 10 | no tack | perfect |
| 9 | trace tack | excellent |
| 8 | very slight tack | very good |
| 7 | slight tack | good/very good |
| 6 | moderate to slight tack | good |
| 5 | moderate tack | fair |
| 4 | very tacky-no seal | poor to fair |

-continued

Blocking Resistance Numerical Ratings

| Blocking Resistance Numerical Ratings | Description of the Separation | Performance Description |
|---|---|---|
| 3 | 5 to 25% seal | poor |
| 2 | 25 to 50% seal | poor |
| 1 | 50 to 75% seal | very poor |
| 0 | 75 to 100% seal | very poor |

Materials

The following materials were used in the Examples herein. Compounds A1 thru A15 and B1 thru B14 refer to the fluoroalcohols listed in Table 1A and Table 1B, respectively.

JEFFAMINE XTJ-580 from Huntsman Chemical, Salt Lake City, Utah, also known as SURFONAMINE L-55, is a monoamine-terminated polyoxyalkylene having ethylene oxide/propylene oxide ratio of about 2.5/7.0 and a molecular weight of about 550.

JEFFAMINE ED-2003 from Huntsman Chemical, also known as XTJ-502, is a polyether diamine based predominately on a polyethylene glycol backbone having about 39 polyethylene glycol (PEG) repeat units to about 6 propylene glycol repeat units and an approximate molecular weight of about 2000.

JEFFAMINE ED-600 from Huntsman Chemical, also known as XTJ-500, is a polyether diamine based predominately on a polyethylene glycol backbone having about 9 PEG repeat units to about 3.6 propylene glycol repeat units and an approximate molecular weight of about 600.

A3-Acrylate

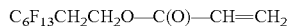
$C_6F_{13}CH_2CH_2O—C(O)—CH=CH_2$

A3-acrylate was prepared from 1H,1H,2H, 2H-perfluoro-1-octanol (Aldrich Chemical Co., Milwaukee, Wis.) using a procedure similar to that for compound A6-acrylate described below.

Compound A6

$C_4F_9CH_2CF_2CH_2CH_2OH$

Ethylene (25 g) was introduced to an autoclave charged with $C_4F_9CH_2CF_2I$ (217 g) and d-(+)-limonene (1 g), and the reactor heated at 240° C. for 12 h. The product was isolated by vacuum distillation to provide $C_4F_9CH_2CF_2CH_2CH_2I$. Fuming sulfuric acid (70 mL) was added slowly to 50 g of $C_4F_9CH_2CF_2CH_2CH_2I$ and mixture was stirred at 60° C. for 1.5 h. The reaction was quenched with ice-cold 1.5 wt % $Na_2SO_3$ aqueous solution and heated at 95° C. for 0.5 h. The bottom layer was separated and washed with 10 wt % aqueous sodium acetate and distilled to provide $C_4F_9CH_2CF_2CH_2CH_2OH$ (compound A6): bp 54-57° C. at 2 mmHg (267 Pascals).

Compound A6-Acrylate

$C_4F_9CH_2CF_2CH_2CH_2O—C(O)—CH=CH_2$ p-Toluene sulfonic acid (p-toluene sulfonic acid, 2.82 g, 0.0148 mol), methylhydroquinone (methylhydroquinone, 420 mg), compound A6 (120 g) and cyclohexane (121 mL) were combined in a flask equipped with Dean Stark trap. The reaction mixture was heated to 85° C., acrylic acid (31.3 mL) was added, and heating continued for 24 h. The Dean Stark trap was replaced with a short path distillation column, deionized water was added to the reaction mixture, followed by distillation of cyclohexane. The reaction mixture was cooled to about 50° C. The bottom layer was placed in a separatory funnel, washed with 10% sodium bicarbonate solution, dried over anhydrous $MgSO_4$, and the solvent evaporated under reduced pressure to provide A6-acylate (134 g, 95% yield): $^1$H NMR (CDCl$_3$, 400 MHz) 6.42 (1H, d-d, J1=17.3 Hz, J2=1.4 Hz), 6.1 (1H, d-d, J1=17.3 Hz, J2=10.5 Hz), 5.87 (1H, d-d, J1=10.5 Hz, J2=1.4 Hz), 4.41 (2H, t, J=6.4 Hz), 2.86~2.48 (2H, m), 2.42 (2H, t-t, J1=16.7 Hz, J2=6.0 Hz); MS: 383 (M$^+$+1).

Compound B3

$C_3F_7OCF_2CF_2I$ (100 g, 0.24 mol) and benzoyl peroxide (3 g) were charged under nitrogen into a vessel. A series of three vacuum/nitrogen gas sequences was then executed at −50° C. and ethylene (18 g, 0.64 mol) was introduced. The vessel was heated for 24 h at 110° C. The autoclave was cooled to 0° C. and opened after degassing. Then the product was collected in a bottle. The product was distilled to provide $C_3F_7OCF_2CF_2CH_2CH_2I$ (80 g, 80% yield): bp 56-60° C. at 25 mm Hg (3325 Pa). A mixture of $C_3F_7OCF_2CF_2CH_2CH_2I$, (300 g, 0.68 mol) and N-methylformamide (300 mL), was heated to 150° C. for 26 h. Then the reaction was cooled to 100° C., followed by the addition of water to separate the crude ester. Ethyl alcohol (77 mL) and p-toluene sulfonic acid (2.59 g) were added to the crude ester, and the reaction was stirred at 70° C. for 15 minutes. Then ethyl formate and ethyl alcohol were distilled out to give a crude product. The crude product was dissolved in ether, washed with aqueous sodium sulfite, water, and brine in turn, then dried over magnesium sulfate. The product was then distilled to provide $C_3F_7OCF_2CF_2CH_2CH_2OH$ (B3, 199 g, 85% yield): bp 71~73° C. at 40 mmHg (5320 Pa).

B3-Acrylate

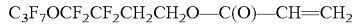
$C_3F_7OCF_2CF_2CH_2CH_2O—C(O)—CH=CH_2$ p-Toluene sulfonic acid (0.34 g), methylhydroquinone (0.026 g), compound B3 (15 g), and cyclohexane (15 mL) were combined in a flask equipped with a Dean Stark trap. The mixture was heated to 85° C., followed by addition of acrylic acid (3.86 mL), and the heating continued 24 h. The Dean Stark trap was replaced with a short path distillation column, deionized water (15 mL) was added, followed by distillation of cyclohexane. The reaction mixture was cooled to about 50° C. and the bottom layer transferred to a separatory funnel, washed with 10% aqueous sodium bicarbonate, dried over anhydrous $MgSO_4$, and concentrated to provide B3-methacylate (14.4 g, 83% yield): $^1$H NMR (CDCl$_3$, 400 MHz) δ 6.43 (1H, d-d, J1=17.3 Hz, J2=1.4 Hz), 6.11 (1H, d-d, J1=17.3 Hz, J2=10.5 Hz), 5.87 (1H, d-d, J1=10.5 Hz, J2=1.4 Hz), 4.43 (2H, t, J=6.4 Hz), 2.42 (2H, t-t, J1=16.7 Hz, J2=6.0 Hz); MS 385 (M$^+$+1).

Bis(3,3,5,5,6,6,7,7,8,8,8-undecafluorooctyl)maleate (A6 maleate)

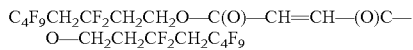
$C_4F_9CH_2CF_2CH_2CH_2O—C(O)—CH=CH—(O)C—O—CH_2CH_2CF_2CH_2C_4F_9$

To a 4 neck 250 mL round bottom flask fitted with stir bar, Dean Stark trap, condenser, and thermocouple, under nitrogen, was added maleic anhydride (2.6 g, 0.027 mol), toluene (100 mL), $C_4F_9CH_2CF_2CH_2CH_2OH$ (17.8 g, 0.054 mol, A6), and p-toluene sulfonic acid (0.5 g, 0.0027 mol). The Dean Stark trap was filled with toluene, and the reaction was heated to reflux. The reaction was monitored by LC/MS and GC. After 6.5 h of reflux an additional 100 mg (0.0003 mol) of A6 was added and the reaction was refluxed for an additional 3.5 h. The mixture was cooled to ambient temperature and diluted with ethyl acetate (50 mL), then washed with saturated sodium bicarbonate (1×25 mL) and saturated sodium chloride (1×25 mL). The organic phase was dried over magnesium sulfate, filtered, and concentrated in vacuo at 40° C., to provide the maleate product as an oil (18.8 g, 94%). GC showed 1 major peak (92%) at 15.3 min for the maleate, with the corresponding fumarate at 15.9 min (4.9%). LC/MS (API-ES+) showed 1 peak at 737 (M+H). $^1$H NMR (400 MHz, CDCl$_3$, δ): 6.26 (s, 2H, =CH), 4.43 (t, 4H, $^3J_{HH}$=6.4 Hz, OCH$_2$), 2.77 (t of t, 4H, $^3J_{HF}$=18.4, 14.0 Hz, CF$_2$CH$_2$CF$_2$), 2.44 (t of t, 4H, $^3J_{HF}$=16.0 Hz, $^3J_{HH}$=6.4 Hz, CH$_2$CH$_2$CF$_2$).

Bis(3,3,4,4,5,5,6,6,6-nonafluorohexyl)maleate (A1 maleate)

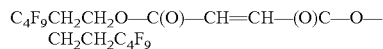

C$_4$F$_9$CH$_2$CH$_2$OH (17.4 g, 0.066 mol, A1) was treated with maleic anhydride (3.2 g, 0.033 mol) in a similar method as described for the synthesis bis(3,3,5,5,6,6,7,7,8,8,8-undecafluorooctyl)maleate to provide the maleate product as an oil (16.4 g, 82%). GC showed 1 major peak (98.4%) at 11.9 min with the corresponding fumarate at 12.5 min (1.6%). LC/MS (API-ES+) showed 1 peak at 608.9 (M+H).

Compound A7

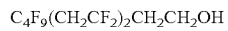

Ethylene (56 g) was introduced to an autoclave charged with C$_4$F$_9$(CH$_2$CF$_2$)$_2$I (714 g) and d-(+)-limonene (3.2 g), and the reactor heated at 240° C. for 12 h. The product was isolated by vacuum distillation to provide C$_4$F$_9$(CH$_2$CF$_2$)$_2$CH$_2$CH$_2$I. A mixture of C$_4$F$_9$(CH$_2$CF$_2$)$_2$CH$_2$CH$_2$I (10 g, 0.02 mol) and N-methylformamide (8.9 mL, 0.15 mol) was heated to 150° C. for 26 h. The mixture was cooled to 100° C., followed by the addition of water to separate the crude ester. Ethyl alcohol (3 mL) and p-toluene sulfonic acid (0.09 g) were added and the mixture stirred at 70° C. for 0.25 h. Ethyl formate and ethyl alcohol were removed by distillation to give a crude product. The crude product was dissolved in ether, washed with 10 wt % aqueous sodium sulfite, water and brine, in turn, and dried over magnesium sulfate. Distillation provided the product A7 (6.5 g, 83% yield): bp 94-95° C. at 2 mm Hg (266 Pascals).

Bis(3,3,5,5,7,7,8,8,9,9,10,10,10-tridecafluorodecyl)maleate (A7 maleate)

C$_4$F$_9$ (CH$_2$CF$_2$)$_2$CH$_2$CH$_2$O—C(O)—CH=CH—(O)C—O—CH$_2$CH$_2$(CF$_2$CH$_2$)$_2$C$_4$F$_9$C$_4$F$_9$(CH$_2$CF$_2$)$_2$CH$_2$CH$_2$OH (18.1 g, 0.046 mol, A7) was treated with maleic anhydride (2.3 g, 0.023 mol) in a similar method as described for the synthesis bis(3,3,5,5,6,6,7,7,8,8,8-undecafluorooctyl)maleate to provide the maleate product as an white solid after recrystallization from 1-chlorobutane/hexanes (18.1 g, 90% yield, mp 35-37° C.): LC/MS (API-ES+) showed 1 peak at 865 (M+H) and 887 (M+Na); $^1$H NMR (400 MHz, CDCl$_3$, δ): 6.27 (s, 2H, =CH), 4.41 (t, 4H, $^3J_{HH}$=6.0 Hz, OCH$_2$), 2.85 (bd quintet, 4H, $^3J_{HF}$=16.0 Hz, CF$_2$CH$_2$CF$_2$), 2.72 (quintet, 4H, $^3J_{HF}$=15.6 Hz, CF$_2$CH$_2$CF$_2$), 2.39 (t of t, 4H, $^3J_{HF}$=16.0 Hz, $^3J_{HH}$=6.4 Hz, CH$_2$CH$_2$CF$_2$).

Bis[3,3,4,4-tetrafluoro-4-(perfluoropropoxy)butyl]maleate (B3 maleate)

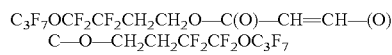

C$_3$F$_7$OCF$_2$CF$_2$CH$_2$CH$_2$OH, (17.8 g, 0.054 mol, B3) was treated with maleic anhydride (2.6 g, 0.027 mol) in a similar method as described for the synthesis bis(3,3,5,5,6,6,7,7,8,8,8-undecafluorooctyl)maleate to provide the maleate product as an oil (16.5 g, 82.5%). GC showed 1 major peak (98%) at 11.8 min and the corresponding fumarate at 12.3 min (1.4%): $^1$H NMR (400 MHz, CDCl$_3$, δ): 6.28 (s, 2H, =CH), 4.47 (t, 4H, $^3J_{HH}$=6.8 Hz, OCH$_2$), 2.46 (t of t, 4H, $^3J_{HF}$=17.6 Hz, $^3J_{HH}$=6.8 Hz, CH$_2$CH$_2$CF$_2$).

EXAMPLES

Examples 1-18

Examples 1-18 illustrate the syntheses of compositions of formula (I) wherein m is 2, n is 0, and A is hydrogen; that is, of generalized formula (Ia) according to Path A in Reaction Scheme 1. For each example the corresponding amount of R$_o$—NH$_2$ and fluorinated acrylate listed in Table 2A, and methylhydroquinone (0.10 g) were mixed together in a vial equipped with a magnetic stirrer and screw cap. The mixture was stirred at 55-60° C. for 24-72 h as listed in Table 2A. The progress of the reactions was monitored by gas chromatography analysis, as described below, to confirm completion of the reaction. In Examples 1-13 the crude product was further purified by extraction by conversion to the acetic acid salt. The sample was transferred to a beaker and mixed with hexane (50 mL). The solution was stirred for 10 min using a magnetic stirrer, followed by addition of acetic acid (2 mL) to separate the product from the hexane layer. The hexane layer (top layer) was removed. Another portion of hexane was added to the bottom layer and the mixture stirred for 1 h followed by removal of the hexane layer. The bottom layer was air-dried to provide the final product as a yellow oil. GC analysis (Agilent 6850, Column: HP-1 Methyl Siloxane Capillary 30.0 m×320 um×0.5 um nominal) with a temperature ramp from 60-250° C., at 15° C./min, a flow rate of 3.5 mL/min, and a flame ionization detector, was used analyze and establish purity of products as listed in Table 2A. In all cases the most significant impurity was the mono-acrylate adduct, as depicted in Reaction Scheme 1, Path A. Compositions of Examples 14-18 were analyzed by GC and NMR without purification by extraction. Several products of Examples 1-18 were characterized by NMR and LC/MS Example 2

$^1$H NMR (500 MHz, d6-THF,): 4.34 (t, 4H, J=6.4 Hz), 3.50 (t, 2H, J=6.0 Hz), 2.73 (t, 4H, J=6.9 Hz), 2.56 (m, 6H), 2.44 (t, 4H, J=7.16), 1.57 (m, 2H, J=6.5 Hz). $^{13}$C NMR (126 MHz, d6-THF,): 171.3, 60.2, 55.8, 51.1, 49.3, 32.2, 29.9, 24.8. LC/MS (API-ES+)=912.1 (M+H).

Example 3

$^1$H NMR (500 MHz, d6-THF,): 4.43 (t, 4H, J=6.4 Hz), 3.54 (m, 1H, J=6.5 Hz), 2.85 (m, 4H), 2.68 (m, 4H), 2.49 (m, 4H), 2.38 (m, 2H), 1.09 (d, 3H, J=5.7 Hz). $^{13}$C NMR (126 MHz, d6-THF,): 171.5, 63.9, 62.5, 55.8, 49.6, 32.2, 30.1, 19.8. LC/MS (API-ES+)=912.1 (M+H).

Example 12

$^1$H NMR (500 MHz, d6-THF,): 4.24 (t, 4H, J=6.5 Hz), 2.63 (t, 4H, J=7.3 Hz), 2.48 (m, 6H), 2.34 (m, 8H), 2.27 (t, 4H, J=6.8 Hz), 1.42 (m, 2H, J=7.0 Hz), 0.86 (t, 6H, J=7.9 Hz). $^{13}$C NMR (126 MHz, d6-THF,): 171.7, 59.6, 56.1, 52.1, 51.2, 49.7, 47.2, 32.7, 30.5, 25.0. LC/MS (API-ES+)=967.3 (M+H).

Example 17

$^1$H NMR (500 MHz, d6-THF,): 4.32 (t, 4H, J=5.7 Hz), 2.72 (t, 4H, J=7.3 Hz), 2.56 (m, 4H), 2.43 (m, 6H), 2.20 (t, 2H, J=7.0 Hz), 1.42 (s, 6H), 1.53 (m, 2H, J=6.7 Hz). $^{13}$C NMR (126 MHz, d6-THF,): 171.7, 57.5, 56.2, 51.8, 49.8, 45.1, 32.7, 30.1, 25.8. LC/MS (API-ES+)=871.2 (M+H).

Pont de Nemours and Company, Wilmington, Del.), containing a mixture of perfluoroalkyl homologues ranging from 2 to 16 carbon atoms, predominantly 6, 8 and 10 carbon atoms. The surface tension was measured in deionized water. The results are listed in Table 2F.

TABLE 2A

Reagents and conditions for twin-tail fluorinated surfactants of formula (Ia)

| Example | $R_a$-NH$_2$ Name | Amt g | Acrylate[a] | Amt g | Time h | Temp° C. | % Yield | % Purity |
|---|---|---|---|---|---|---|---|---|
| 1 | 1-ethanolamine | 0.61 | A3 | 10.4 | 24 | 58 | 81 | 89 |
| 2 | 1-propanolamine | 0.75 | A3 | 10.4 | 24 | 58 | 81 | 92 |
| 3 | 2-propanolamine | 0.75 | A3 | 10.4 | 24 | 60 | 64 | 90 |
| 4 | 2-methoxyethylamine | 0.75 | A3 | 10.4 | 24 | 60 | 60 | 91 |
| 5 | 1-butanolamine | 0.89 | A3 | 10.4 | 24 | 60 | 75 | 92 |
| 6 | 1-pentanolamine | 1.0 | A3 | 10.4 | 24 | 58 | 77 | 90 |
| 7 | 2-ethoxyethanolamine | 1.0 | A3 | 10.4 | 24 | 58 | 75 | 92 |
| 8 | 1-hexanolamine | 1.2 | A3 | 10.4 | 24 | 63 | 81 | 89 |
| 9 | N,N-dimethylethylamine | 0.88 | A3 | 10.4 | 24 | 58 | 80 | 88 |
| 10 | N,N-dibutylpropylamine | 1.9 | A3 | 10.4 | 36 | 63 | 81 | 90 |
| 11 | N,N-dimethylpropylamine | 1.0 | A3 | 10.4 | 24 | 58 | 84 | 92 |
| 12 | N,N-diethylpropylamine | 1.3 | A3 | 10.4 | 36 | 63 | 88 | 88 |
| 13 | N,N-dimethylbutylamine | 1.2 | A3 | 10.4 | 36 | 60 | 80 | 92 |
| 14 | Jeffamine XTJ 580 | 5.5 | A3 | 9.8 | 72 | 65 | NP | 81[b] |
| 15 | N,N-dimethylpropylamine | 1.0 | A6 | 8.0 | 48 | 60 | NP | 90 |
| 16 | Jeffamine XTJ 580 | 5.5 | A6 | 8.0 | 72 | 65 | NP | 75[b] |
| 17 | N,N-dimethylpropylamine | 1.0 | B3 | 8.1 | 48 | 60 | NP | 92 |
| 18 | Jeffamine XTJ 580 | 5.5 | B3 | 8.1 | 72 | 65 | NP | 75[b] |

[a]Acrylate of alcohol prepared as described above under "Materials".
[b]purity determined by $^1$H NMR.
NP = indicates that no purification was performed; therefore, all the material recovered was used as product.

Examples 14, 16 and 18 prepared using JEFFAMINE XTJ 580 were further characterized by size exclusion chromatography (SEC) to monitor their increase in average molecular weight as results of the double Michael Addition reaction. Table 2B shows the results for Examples 14, 16, and 18.

TABLE 2B

Average M$_w$ for Examples 14, 16, and 18

| Sample | Average Mw Calculated | Average Mw By SEC | Polydispersity |
|---|---|---|---|
| JEFFAMINE XTJ 580 | 550 | 567 | 1.177 |
| 14 | 1386 | 1694 | 1.058 |
| 16 | 1314 | 1683 | 1.052 |
| 18 | 1318 | 1641 | 1.068 |

Test Method 1A was used to measure surface tension of acidic solutions of Examples 1-18. A 1% by weight solution of each surfactant was prepared by mixing 1.0 g of the product of the particular Example, 1.0 g of acetic acid and 98.0 g of deionized water in a beaker. The mixture was then sonicated for 4 min at maximum power using a VIRSONIC 600 model 408912 sonicator available from Biopharm Process Systems, Ltd., Winchester, UK. A dilution series was prepared using deionized water. The resulting solutions were mixed well using magnetic stirrer bar and the surface tension measured. The results are listed in Tables 2C, 2D and 2E.

Comparative Example A

Comparative Example A consisted of a fluoroalkyl ethoxylate surfactant (commercially available from E. I. du

TABLE 2C

| | Surface tension (mN/m) | | | | | |
|---|---|---|---|---|---|---|
| Example | 1 | 2 | 3 | 4 | 5 | 6 |
| Conc. (wt %) | | | | | | |
| 0.001 | 47.9 | 23.1 | 43.1 | 36.2 | 20.0 | 53.50 |
| 0.005 | 29.1 | 18.2 | 14.0 | 13.6 | 19.3 | 47.3 |
| 0.01 | 21.8 | 18.6 | 15.0 | 13.8 | 18.9 | 28.3 |
| 0.05 | 16.1 | 18.8 | 17.7 | 16.2 | 18.9 | 22.0 |
| 0.1 | 17.9 | 18.8 | 17.3 | 16.3 | 18.9 | 18.3 |

TABLE 2D

| | Surface tension (mN/m) | | | | | | |
|---|---|---|---|---|---|---|---|
| Example | 7 | 8 | 9 | 10 | 11 | 12 | 13 |
| Conc. (wt %) | | | | | | | |
| 0.001 | 63.8 | 17.5 | 18.0 | 46.4 | 19.0 | 18.0 | 35.1 |
| 0.005 | 16.6 | 18.0 | 17.0 | 23.3 | 14.8 | 17.2 | 20.6 |
| 0.01 | 14.8 | 18.0 | 16.4 | 16.7 | 17.2 | 17.7 | 21.4 |
| 0.05 | 16.6 | 19.3 | 18.0 | 19.1 | 17.2 | 16.8 | 18.3 |
| 0.1 | 18.5 | 20.4 | 17.7 | 19.4 | 17.4 | 17.8 | 18.2 |

TABLE 2E

| Example Conc. (wt %) | Surface tension (mN/m) | | | | |
|---|---|---|---|---|---|
| | 14 | 15 | 16 | 17 | 18 |
| 0.001 | 30.9 | 31.5 | 41.3 | 21.2 | 43.0 |
| 0.005 | 22.0 | 23.5 | 27.2 | 20.8 | 24.6 |
| 0.01 | 20.3 | 24.6 | 24.6 | 20.6 | 20.5 |
| 0.05 | 20.0 | 22.1 | 25.2 | 18.1 | 20.7 |
| 0.1 | 20.3 | 20.7 | 25.5 | 17.1 | 21.1 |

TABLE 2F

Comparative Example A

| Concentration (wt %) | Surface Tension (mN/m) |
|---|---|
| 0.001 | 51.9 |
| 0.005 | 27.0 |
| 0.01 | 25.0 |
| 0.05 | 20.1 |
| 0.1 | 20.0 |

Comparison of the surface tensions of Examples 1-18 with Comparative Example A indicated that the Examples 1-18 exhibited a surface tension comparable to, and in many cases, lower than, that of the commercial product Comparative Example A at the same weight % concentration. Examples 1-18 contained perfluoroalkyl groups having 3 to 6 carbon atoms versus 2 to 16 carbon atoms for Comparative Example A, and thus Examples 1-5 and 7-18 contained a lower level of fluorine.

Furthermore Table 2G compares the performance of the surfactants of Examples 1-13 with Comparative Example A in terms of weight % concentration needed to lower the surface tension of water to 20 mN/m or below.

TABLE 2G

Concentration of surfactant to achieve surface tension of 20 mN/m

| Example | Concentration (wt %) | % F (10$^{-4}$) |
|---|---|---|
| Comparative A | 0.05 | 210 |
| 1 | 0.05 | 55 |
| 2 | 0.005 | 14 |
| 3 | 0.005 | 14 |
| 4 | 0.005 | 14 |
| 5 | 0.005 | 5 |
| 6a | 0.05 | 265 |
| 7 | 0.005 | 27 |
| 8 | 0.001 | 5 |
| 9 | 0.001 | 5 |
| 10 | 0.01 | 48 |
| 11 | 0.001 | 5 |
| 12 | 0.001 | 5 |
| 13 | 0.005 | 13 |

$^a$surface tension was 22 mN/m

Examples 1-18 provided comparable performance to Comparative Example A generally using lower levels of fluorine.

Examples 2-5 and 7-13 exhibited the desired 20 mN/m surface tension at weight % concentrations that are 5 to 50 times lower than that of Comparative Example A. Example 1 was comparable to the performance of Comparative Example A, whereas Example 6 required a higher concentration to achieve the desired surface tension. Thus, the compositions of the invention provide comparable surfactant properties at significantly lower weight % concentrations and thus significantly lower weight % fluorine.

Surface tension of compositions of Examples 14, 16 and 18 in slightly acidic media and neutral media was measured over a three-week period of time at ambient temperature. The results are listed in Tables 3A, 3B and 3C.

TABLE 3A

Stability of surface tension of Example 14

| | Surface Tension (mN/m) | | | | | |
|---|---|---|---|---|---|---|
| | initial | | 7 days | | 21 days | |
| Conc. (wt %) | Neutral | Acidic | Neutral | Acidic | Neutral | Acidic |
| 0.5 | 27.9 | 20.3 | 22.3 | 20.5 | 19.2 | 22.5 |
| 0.1 | 29.7 | 20.3 | 32.3 | 21.0 | 29.4 | 23.2 |
| 0.05 | 31.4 | 20.0 | 30.0 | 20.0 | 31.5 | 26.9 |
| 0.01 | 41.0 | 20.3 | 37.8 | 29.2 | 39.8 | 34.2 |
| 0.005 | 45.7 | 22.0 | 43.0 | 30.5 | 40.3 | 33.2 |
| 0.0025 | 48.6 | 30.6 | 37.9 | 34.5 | 37.3 | 40.6 |
| 0.001 | 49.2 | 30.9 | 42.6 | 36.7 | 35.4 | 41.7 |

TABLE 3B

Stability of surface tension of Example 16

| | Surface Tension (mN/m) | | | | | |
|---|---|---|---|---|---|---|
| | initial | | 7 days | | 21 days | |
| Conc. (wt %) | Neutral | Acidic | Neutral | Acidic | Neutral | Acidic |
| 0.5 | 23.1 | 23.3 | 20.8 | 22.7 | 20.0 | 21.5 |
| 0.1 | 26.2 | 25.5 | 24.8 | 25.4 | 22.8 | 25.6 |
| 0.05 | 26.7 | 25.2 | 25.8 | 25.3 | 25.3 | 25.3 |
| 0.01 | 33.7 | 24.5 | 42.5 | 24.3 | 36.5 | 25.2 |
| 0.005 | 47.0 | 27.2 | 44.3 | 26.3 | 34.9 | 26.3 |
| 0.0025 | 49.3 | 27.5 | 45.3 | 25.2 | 46.5 | 29.4 |
| 0.001 | 50.7 | 41.3 | 47.2 | 32.1 | 39.8 | 33.2 |

TABLE 3C

Stability of surface tension of Example 18

| | Surface Tension (mN/m) | | | | | |
|---|---|---|---|---|---|---|
| | initial | | 7 days | | 21 days | |
| Conc. (wt %) | Neutral | Acidic | Neutral | Acidic | Neutral | Acidic |
| 0.5 | 24.6 | 22.1 | 23.4 | 22.1 | 21.4 | 22.9 |
| 0.1 | 27.2 | 21.1 | 30.3 | 21.6 | 30.4 | 22.4 |
| 0.05 | 27.9 | 20.7 | 37.8 | 21.0 | 32.1 | 22.5 |
| 0.01 | 33.7 | 20.5 | 38.5 | 21.0 | 36.0 | 25.1 |
| 0.005 | 36.1 | 24.6 | 39.5 | 25.5 | 39.4 | 27.4 |
| 0.0025 | 36.0 | 33.1 | 42.1 | 24.3 | 35.1 | 29.7 |
| 0.001 | 49.9 | 43.0 | 48.2 | 40.8 | 34.1 | 32.7 |

The results listed in Tables 3A, 3B and 3C indicated that the surface tension of compositions of Examples 14, 16 and 18 had the following order of stability: 16>18>14 in acidic media. For instance, Example 14 at 0.01 weight % increased from 20.3 to 34.2 mN/m over 21 days in acidic media; whereas Example 16, under the same conditions increased from 24.5 to 25.2 mN/m. The results indicated that compositions of formula (I) wherein the structure of $R_f$ may vary, had the following order of stability: (IIb)>(IIc)>(IIa).

The compositions of Examples 14, 16 and 18 were tested according to Test Method 3 for open-time extension in interior/exterior 100% acrylic house paint (Vista 6400 available from Vista Paint Corporation, Fullerton, Calif.). The house paint was formulated by the manufacturer without the usual 2 weight % propylene glycol. The compositions of each Example were blended into the house paint at 0.1 weight % level along with 2 weight % propylene glycol. The test results are listed in Table 4A.

TABLE 4A

Interior/Exterior 100% Acrylic Open-Time Extension

| Example | Open Time Extension (min) | % Extension |
|---|---|---|
| 14 | 3 | 7.0 |
| 16 | 3 | 7.9 |
| 18 | 3 | 6.8 |

The data in Table 4A demonstrates that adding the compositions of the present invention to a conventional paint increased the open time extension versus the same paint with no composition of the present invention added.

Compositions of Examples 14, 16 and 18 were added to Vista semi-gloss latex paint (Vista Paint Corporation, Fullerton, Calif.) in an amount of 0.222 weight % by dry weight of the composition in the wet paint and tested for resistance to blocking using Test Method 4. Resulting data are in Table 4B.

TABLE 4B

Resistance to Blocking[a] in Semi-gloss Latex Paint

| Example | Blocking Rating |
|---|---|
| Untreated Control | 1.3 |
| 14 | 4.7 |
| 16 | 4.0 |
| 18 | 5.0 |

[a]An average of 3 replicates is reported.

According to the results in Table 4B, fair resistance to blocking was demonstrated for products containing Examples 14, 16 and 18.

Example 19

Bis(3,3,5,5,6,6,7,7,8,8,8-undecafluorooctyl)maleate (5.7 g 0.0078 mol, 1 eq) and JEFFAMINE XTJ-580 (4.3 g, 0.0078 mol, 1 eq) were mixed, heated to an interior temperature (immersion thermocouple) of about 50° C. using an oil bath, and stirred for 8.5 h under nitrogen atmosphere with monitoring by LC/MS and GC. The mixture was poured into a bottle to provide a yellow oil (8.8 g, 88%). LC/MS (API-ES+) showed 1 broad peak that displayed the expected product distribution in the mass spectrum. Surface tension was measured in MILLIPORE filtered water (Millipore Corporation, Billerica, Mass.) according to Test Method 1B, and the results are listed in Table 5A. The surface tension of Comparative Example A was measured using Test Method 1B and the results are listed in Table 5B.

TABLE 5A

Surface Tension for Example 19

| Concentration (wt %) | Surface Tension (mN/m) | Std. Dev. (mN/m) |
|---|---|---|
| 0 | 72.1 | 0.1 |
| 0.0001 | 47.4 | 0.1 |
| 0.001 | 20.7 | 0.1 |
| 0.01 | 19.5 | 0.1 |
| 0.1 | 18.9 | 0.1 |

TABLE 5B

Surface Tension for Comparative Example A

| Concentration (wt %) | Surface Tension (mN/m) | Std. Dev. (mN/m) |
|---|---|---|
| 0.0001 | 72.45 | 0.15 |
| 0.001 | 38.42 | 0.35 |
| 0.01 | 21.20 | 0.36 |
| 0.1 | 18.38 | 0.03 |
| 0.5 | 18.36 | 0.02 |

Comparison of surface tension of Example 19 in Table 5A versus that of Comparative Example A in Table 5B indicates that the composition of Example 19 had significantly lower surface tension than the Comparative Example A at 0.01 weight % and in particular at 0.001 weight % concentration.

Example 20

Bis(3,3,4,4,5,5,6,6,6-nonafluorohexyl)maleate (5.3 g, 0.0086 mol, 1 eq) and JEFFAMINE XTJ-580 (4.7 g, 0.0086 mol, 1 eq) were mixed, heated to an interior temperature of about 50° C. using an oil bath, and stirred for 26.5 h under nitrogen atmosphere with monitoring by LC/MS and GC. The mixture was poured into a bottle to provide a yellow oil (8.8 g, 88%). LC/MS (API-ES+) showed 1 broad peak that displayed the expected product distribution in the mass spectrum. Surface tension measurements were obtained in 10 weight % isopropanol (IPA) in water for both Example 20 and Comparative Example A according to Test Method 1B, and the results are listed in Tables 6A and 6B.

TABLE 6A

Surface Tension for Example 20

| Concentration (wt %) | Surface Tension (mN/m) | Std. Dev. (mN/m) |
|---|---|---|
| 0 | 39.72 | 0.04 |
| 0.001 | 19.34 | 0.08 |
| 0.0025 | 19.06 | 0.03 |
| 0.005 | 18.94 | 0.02 |
| 0.01 | 18.86 | 0.01 |
| 0.05 | 18.79 | 0.02 |
| 0.1 | 18.78 | 0.01 |
| 0.5 | 18.66 | 0.01 |

TABLE 6B

Surface Tension for Comparative Example A

| Concentration (wt %) | Surface Tension (mN/m) | Std. Dev. (mN/m) |
|---|---|---|
| 0 | 40.0 | 0.1 |
| 0.0001 | 39.6 | 0.1 |
| 0.001 | 35.1 | 0.1 |
| 0.01 | 21.7 | 0.1 |

TABLE 6B-continued

Surface Tension for Comparative Example A

| Concentration (wt %) | Surface Tension (mN/m) | Std. Dev. (mN/m) |
|---|---|---|
| 0.1 | 20.3 | 0.1 |
| 0.5 | 19.6 | 0.1 |

Comparison of surface tension data of Example 20 in Table 6A versus Comparative Example A in Table 6B indicates that the composition of Example 20 had significantly lower surface tension than the Comparative Example A at 0.01 weight % and in particular at 0.001 weight % concentration.

Example 21

Bis(3,3,4,4-tetrafluoro-4-(perfluoropropoxy)butyl)maleate (5.7 g, 0.0078 mol, 1 eq) and JEFFAMINE XTJ-580 (4.3 g (0.0078 mol, 1 eq) were mixed, heated to an interior temperature of about 50° C. using an oil bath, and stirred for 21.5 h under nitrogen atmosphere with monitoring by LC/MS and GC. The mixture was poured into a bottle to provide a yellow oil (8.8 g, 88%). LC/MS (API-ES+) shows 1 broad peak that displays the expected product distribution in the mass spectrum. Surface tension measurements were obtained in MILLIPORE filtered water according to Test Method 1B, and the results are listed in Table 7.

TABLE 7

Surface Tension for Example 21 in Water

| Concentration (wt %) | Surface Tension (mN/m) | Std. Dev. (mN/m) |
|---|---|---|
| 0 | 72.5 | 0.1 |
| 0.0001 | 52.2 | 0.1 |
| 0.001 | 24.6 | 0.1 |
| 0.01 | 17.9 | 0.1 |
| 0.1 | 17 | 0.1 |

Comparison of surface tension data of Example 21 in Table 7 versus that of Comparative Example A in Table 5B indicates that the composition of Example 21 had significantly lower surface tension than the Comparative Example A at 0.001 and 0.01 weight % concentration.

Example 22

Bis(3,3,5,5,7,7,8,8,9,9,10,10,10-tridecafluorodecyl)maleate (2.4 g, 0.0028 mol, 1 eq), JEFFAMINE XTJ-580 (1.6 g, 0.0028 mol, 1 eq) and dry acetonitrile (2 g) were mixed in a 10 mL REACTI-VIAL reaction vials (Fisher Scientific, Pittsburgh Pa.), placed in a 70° C. reactor block, and stirred for 93 h with monitoring by LC/MS and GC. The mixture was concentrated at 35° C., poured into a bottle to provide a brown oil (3.4 g, 85%): LC/MS (API-ES+) showed 1 broad peak (80% by MS integration) that displayed the expected product distribution in the mass spectrum. Surface tension measurements were obtained in MILLIPORE filtered water according to Test Method 1B, and the results are listed in Table 8.

TABLE 8

Surface Tension for Example 22 in Water

| Concentration (wt %) | Surface Tension (mN/m) | Std. Dev. (mN/m) |
|---|---|---|
| 0 | 72.1 | 0.1 |
| 0.0001 | 59.5 | 0.1 |
| 0.001 | 48.6 | 0.1 |
| 0.01 | 19.9 | 0.1 |
| 0.1 | 19.3 | 0.1 |

Comparison of surface tension data of Example 22 in Table 8 versus that of Comparative Example A in Table 5B indicates that the composition of Example 22 had surface tension comparable to the commercial surfactant at 0.01 wt % concentration.

Table 9A compares the weight % fluorine for Examples 19-22 with Comparative Example A, a commercial surfactant, showing that at the same weight % concentration (0.01 wt %), Comparative Example A had significantly higher weight % fluorine than the examples of the invention.

TABLE 9A

Wt % Fluorine for Examples 19-22 and Comparative Example A

| Example | wt % | wt % F ($10^{-4}$) |
|---|---|---|
| Comparative A | 0.01 | 42 |
| 19 | 0.01 | 34 |
| 20 | 0.01 | 28 |
| 21 | 0.01 | 34 |
| 22 | 0.01 | 35 |

Compositions of Examples 14, 16, 18, and 19-21 were tested for performance as a wetting and leveling agent in a commercial floor polish according to Test Method 2. In a control the same polish was used with no leveling agent was added. Two commercial surfactants, Comparative Example A as described above and Comparative Example B as described below were measured for comparison. All samples where measured at 75 ppm (micrograms/g) loading and at the same time to nullify potential variations in room humidity and temperature. The results are listed in Table 9B.

Comparative Example B

Comparative Example B was a commercial surfactant available from E. I. du Pont de Nemours and Company, Wilmington, Del. It is a blend of a fluoroalkyl phosphate ammonium salt and a hydrocarbon surfactant. The phosphate salt contains a mixture of perfluoroalkyl homologues, ranging from 2 to 16 carbon atoms, predominantly 6, 8 and 10 carbon atoms.

TABLE 9B

Ratings for Wetting and Leveling Test

| | Rating Coating No. | | | | | |
|---|---|---|---|---|---|---|
| Example | 1 | 2 | 3 | 4 | 5 | average |
| Control | 2 | 1 | 1 | 1 | 1 | 1.2 |
| Comparative A | 3 | 4 | 4 | 4 | 4 | 3.8 |
| Comparative B | 3 | 4 | 4 | 4 | 4 | 3.8 |

TABLE 9B-continued

Ratings for Wetting and Leveling Test

| | Rating Coating No. | | | | | |
|---|---|---|---|---|---|---|
| Example | 1 | 2 | 3 | 4 | 5 | average |
| 14 | 2 | 1 | 1 | 1 | 1 | 1.2 |
| 16 | 2 | 2 | 1 | 1 | 1 | 1.4 |
| 18 | 2 | 1 | 1 | 1 | 1 | 1.2 |
| 19 | 4 | 4.5 | 4.5 | 4.5 | 4 | 4.3 |
| 20 | 3 | 4 | 4 | 4 | 4 | 3.8 |
| 21 | 3 | 4 | 4 | 4 | 4 | 3.8 |

The results indicate that the compositions of Examples 19-21 showed wetting and leveling characteristics comparable or better in performance than the Comparative Examples A and B. Examples 19-21 have less overall fluorine present due to the shorter perfluoroalkyl chains present, yet provide the same of better performance.

Examples 23 to 27

The following Examples 23 to 27 illustrate the formation of surfactants by addition of two equivalents of maleate ester to a diamine according to Reaction Scheme 1, Path B. In a REACTI-VIAL reaction vial, one equivalent of JEFFAMINE diamine and 2 equivalents of maleate ester as listed in Table 10 were combined and heated in a reactor block about 5 days at 50° C., 4 days at 60° C., and 1.5 days at 70° C. to ensure at least 80% conversion to product as assessed by end-group analysis in the $^1$H NMR spectrum. Since the reaction mixture was very viscous, a few mL of acetonitrile was added to facilitate stirring in Example 26. In Example 25 a small amount of a second unidentified phase became visible, which was decanted prior to product isolation.

TABLE 10

| | $NH_2-R_0-NH_2$ | | Maleate[a] | | Product | | |
|---|---|---|---|---|---|---|---|
| Example | Name JEFFAMINE | Amt g | | Amt g | g | % yield | appearance |
| 23 | ED-2003 | 2.3 | A6 | 1.7 | 2.9 | 73 | brown oil |
| 24 | ED-2003 | 2.5 | A1 | 1.5 | 3.0 | 75 | brown semi-solid |
| 25 | ED-2003 | 2.3 | B3 | 1.7 | 3.0 | 75 | dark yellow semi-solid |
| 26 | ED-2003 | 2.1 | A7 | 1.9 | 3.7 | 92 | brown semi-solid |
| 27 | ED-600 | 1.0 | A7 | 3.0 | 4.0 | 100 | brown oil |

[a]Prepared as previously described under "Materials"

The surface tension measurements for Examples 23-27 were obtained in accordance with Test Method 1B with the following exceptions. The Example solutions were initially prepared at 0.1 weight % concentrations and diluted in series. Each Example (0.04 g) was added to a sterile vial, then deionized water was added to balance to 40.0 g, and then the vial was gently stirred until a fully dissolved solution had formed. The solution was then sonicated for approximately 2 minutes to enhance dispersion and remove bubbles. The dilutions for each series were prepared in an analogous manner. Example 27 was dissolved in 10% acetonitrile in deionized water for the 0.1 weight % solution concentration and dilution was performed with deionized water. The results are listed in Table 11.

TABLE 11

Surface Tension for Example 23-27 in Water

| Example | Concentration (wt %) | Surface Tension (mN/m) |
|---|---|---|
| 23 | 0 | 72.2 |
| | 0.0001 | 61.8 |
| | 0.001 | 38.7 |
| | 0.01 | 32.4 |
| | 0.1 | 28.2 |
| 24 | 0 | 72.4 |
| | 0.0001 | 57.8 |
| | 0.001 | 34.5 |
| | 0.01 | 22.0 |
| | 0.1 | 21.1 |
| 25 | 0 | 72.2 |
| | 0.0001 | 62.7 |
| | 0.001 | 47.9 |
| | 0.01 | 32.2 |
| | 0.1 | 28.3 |
| 26 | 0 | 72.6 |
| | 0.0001 | 62.5 |
| | 0.001 | 47.1 |
| | 0.01 | 36.0 |
| | 0.1 | 32.3 |
| 27[a] | 0 | 72.5 |
| | 0.0001 | 64.9 |
| | 0.001 | 54.8 |
| | 0.01 | 24.1 |
| | 0.1 | 22.6 |

[a]Example 27 was dissolved in 10% acetonitrile in deionized water

Compositions of Examples 24 and 25 were tested for performance as a wetting and leveling agent in a commercial floor polish according to Test Method 2. In a control no leveling agent was added. Comparative Example A in the same floor polish was measured for comparison. All samples were measured at 75 ppm (microgram/g) loading and at the same time to nullify potential variations in room humidity and temperature. The results are listed in Table 12, with a higher rating indicating superior performance.

TABLE 12

Ratings for Wetting and Leveling Test

| | Rating Coating No. | | | | | |
|---|---|---|---|---|---|---|
| Example | 1 | 2 | 3 | 4 | 5 | average |
| Control | 2 | 1 | 1 | 1 | 1 | 1.2 |
| Comparative A | 3 | 4 | 4 | 4 | 3 | 3.6 |
| 24 | 3 | 4 | 4 | 4 | 3 | 3.6 |
| 25 | 4 | 4.5 | 4.5 | 4 | 3 | 4.0 |

The results indicate that the compositions of Examples 24 and 25 showed wetting and leveling characteristics comparable or better in performance than Comparative Example A. The Examples contained less fluorine due to shorter perfluoroalkyl chain lengths than Comparative Example A.

What is claimed is:

1. A composition of formula (I)

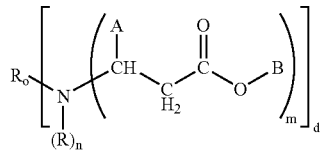

wherein
- m and d are each independently an integer of 1 or 2;
- n is independently 0 or 1;
- each R is independently hydrogen or a $C_1$ to $C_4$ alkyl group;
- A is independently hydrogen or —C(O)—O—B;
- $R_o$ is a linear, branched or cyclic aliphatic group, or combination thereof, having from about 2 to about 100 carbon atoms, interrupted or substituted by 1 to about 50 hydrophilic groups, said hydrophilic groups selected from the group consisting of hydroxyl, amino, ether and mixtures thereof; wherein the ratio of hydrophilic groups to carbon atoms is from about 1:1.1 to about 1:10, each carbon atom has at most one hydrophilic group bonded to it, and covalent bonding between hydrophilic groups is absent;
- each B is independently a monovalent group of formula (IIa), (IIb) or (IIc):

$R_f^1(CH_2)_t(R^1)_r$—     (IIa)

$R_f^2(CH_2CF_2)_p(CH_2CH_2)_q(R^1)_r$—     (IIb)

$R_f^3O(CF_2CF_2)_p(CH_2CH_2)_q(R^1)_r$—     (IIc)

wherein
- each of $R_f^1$ and $R_f^2$ are $C_1$-$C_6$ linear or branched perfluoroalkyl;
- $R_f^3$ is a $C_1$ to $C_7$ linear or branched perfluoroalkyl group, optionally interrupted by one, two or three ether oxygen atoms;
- t is an integer of 1 to about 10;
- p and q are each independently integers of 1 to about 3;
- r is 0 or 1;
- $R^1$ is a divalent radical selected from —S(CH$_2$)$_t$—; and
provided that
- when m is 1, n is 1;
- when m is 2, n is 0, A is hydrogen, and d is 1; and
- when d is 2, m is 1, A is —C(O)—O—B, $R_o$ has at least three carbon atoms, and nitrogens and hydrophilic groups are bonded to different carbon atoms.

2. The composition of claim 1 wherein m is 1, n is 1, and A is —C(O)—O—$R_f$.

3. The composition of claim 1 wherein m is 2, n is 0, and A is hydrogen.

4. The composition of claim 1 wherein the nitrogen is from about 40 mol % to 100 mol % salinized.

5. The composition of claim 1 wherein $R_o$ is a linear, branched or cyclic aliphatic group, or combination thereof, having 2 to about 10 carbon atoms, interrupted or substituted by one hydroxyl, ether or tertiary amino group.

6. The composition of claim 1 wherein $R_o$ is a linear or branched aliphatic group, or combination thereof, having from about 10 to about 100 carbon atoms, interrupted by from about 5 to about 50 ether oxygen toms, wherein the ratio of ether oxygen atoms to carbon atoms is about 1:2 to about 1:3, and wherein each carbon atom has at most one ether oxygen atom bonded to it, and covalent bonding between ether oxygen atoms is absent.

7. The composition of claim 2 wherein $R_o$ a linear or branched aliphatic group, or combination thereof, having from about 10 to about 100 carbon atoms, interrupted by from about 5 to about 50 ether oxygen toms, wherein the ratio of ether oxygen atoms to carbon atoms is about 1:2 to about 1:3, and wherein each carbon atom has at most one ether oxygen atom bonded to it, and covalent bonding between ether oxygen atoms is absent.

8. The composition of claim 1 wherein B is formula (IIa)

$R_f^1(CH_2)_t(R^1)_r$—     (IIa)

9. The composition of claim 8 wherein $R_f^1$ is $C_4$ to $C_6$ linear or branched perfluoroalkyl; t is 2 to 4; and r is 0.

10. The composition of claim 1 wherein B is formula (IIb)

$R_f^2(CH_2CF_2)_p(CH_2CH_2)_q(R^1)_r$—     (IIb)

11. The composition of claim 10 wherein $R_f^2$ is a $C_4$ to $C_6$ linear or branched perfluoroalkyl; p and q are each independently 1 or 2; and r is 0.

12. The composition of claim 1 wherein B is formula (IIc)

$R_f^3O(CF_2CF_2)_p(CH_2CH_2)_q(R^1)_r$—     (IIc)

13. The composition of claim 12 wherein $R_f^3$ is a $C_3$ to $C_7$ linear or branched perfluoroalkyl, optionally interrupted by one, two or three ether oxygen atoms; p and q are each independently 1 or 2; and r is 0.

14. A method of lowering surface tension of a medium comprising contacting the medium with a composition of formula (I)

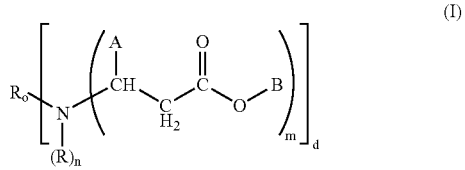

wherein
- m and d are each independently an integer of 1 or 2;
- n is independently 0 or 1;
- each R is independently hydrogen or a $C_1$ to $C_4$ alkyl group;
- A is independently hydrogen or —C(O)—O—B;
- $R_o$ is a linear, branched or cyclic aliphatic group, or combination thereof, having from about 2 to about 100 carbon atoms, interrupted or substituted by 1 to about 50 hydrophilic groups, said hydrophilic groups selected from the group consisting of hydroxyl, amino, ether and mixtures thereof; wherein the ratio of hydrophilic groups to carbon atoms is from about 1:1.1 to about 1:10, each carbon atom has at most one hydrophilic group bonded to it, and covalent bonding between hydrophilic groups is absent;
- each B is independently a monovalent group of formula (IIa), (IIb) or (IIc):

$R_f^1(CH_2)_t(R^1)_r$—     (IIa)

$R_f^2(CH_2CF_2)_p(CH_2CH_2)_q(R^1)_r$—     (IIb)

$R_f^3O(CF_2CF_2)_p(CH_2CH_2)_q(R^1)_r$—     (IIc)

wherein
each of $R_f^1$ and $R_f^2$ are $C_1$-$C_6$ linear or branched perfluoroalkyl;
$R_f^3$ is a $C_1$ to $C_7$ linear or branched perfluoroalkyl group, optionally interrupted by one, two or three ether oxygen atoms;
t is an integer of 1 to about 10;
p and q are each independently integers of 1 to about 3;
r is 0 or 1;
$R^1$ is a divalent radical selected from —S(CH$_2$)$_t$—; and
provided that
when m is 1, n is 1;
when m is 2, n is 0, A is hydrogen, and d is 1; and
when d is 2, m is 1, A is —C(O)—O—B, $R_o$ has at least three carbon atoms, and nitrogens and hydrophilic groups are bonded to different carbon atoms.

15. The method of claim 14 wherein the medium is a coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor polish, or bonding agent.

16. The method of claim 14 wherein the composition of formula (I) is applied to a substrate prior to contacting with the medium.

17. A method of providing resistance to blocking, open time extension, and improved leveling to a coated substrate comprising adding to the coating base prior to deposition on the substrate, a composition comprising one or more compounds of formula (I)

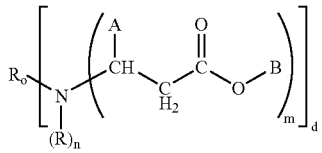
(I)

wherein
m and d are each independently an integer of 1 or 2;
n is independently 0 or 1;
each R is independently hydrogen or a $C_1$ to $C_4$ alkyl group;
A is independently hydrogen or —C(O)—O—B;
$R_o$ is a linear, branched or cyclic aliphatic group, or combination thereof, having from about 10 to about 100 carbon atoms, interrupted by from about 5 to about 50 ether oxygen atoms, wherein the ratio of ether oxygen atoms to carbon atoms is from about 1:2 to about 1:3, and wherein each carbon atom has at most one ether oxygen atom bonded to it, and covalent bonding between ether oxygen atoms is absent;
each B is independently a monovalent group of formula (IIa), (IIb) or (IIc):

$$R_f^1(CH_2)_t(R^1)_r— \qquad (IIa)$$

$$R_f^2(CH_2CF_2)_p(CH_2CH_2)_q(R^1)_r— \qquad (IIb)$$

$$R_f^3O(CF_2CF_2)_p(CH_2CH_2)_q(R^1)_r— \qquad (IIc)$$

wherein
each of $R_f^1$ and $R_f^2$ are $C_1$-$C_6$ linear or branched perfluoroalkyl;
$R_f^3$ is a $C_1$ to $C_7$ linear or branched perfluoroalkyl group, optionally interrupted by one, two or three ether oxygen atoms;
t is an integer of 1 to about 10;
p and q are each independently integers of 1 to about 3;
r is 0 or 1;
$R^1$ is a divalent radical selected from —S(CH$_2$)$_t$—; and
provided that
when m is 1, n is 1;
when m is 2, n is 0, A is hydrogen, and d is 1; and
when d is 2, m is 1, A is —C(O)—O—B, $R_o$ has at least three carbon atoms, and nitrogens and hydrophilic groups are bonded to different carbon atoms.

18. The method of claim 17 wherein the coating composition is a water-dispersed coating, alkyd coating, Type I urethane coating, unsaturated polyester coating, or floor polish.

19. A substrate treated according to the method of claim 14.

20. A substrate to which has been applied a composition of claim 1.

* * * * *